(12) United States Patent
Nakamura

(10) Patent No.: US 12,295,638 B2
(45) Date of Patent: May 13, 2025

(54) DRIVE DEVICE

(71) Applicant: OLYMPUS CORPORATION, Tokyo (JP)

(72) Inventor: Hiroto Nakamura, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 812 days.

(21) Appl. No.: 17/529,991

(22) Filed: Nov. 18, 2021

(65) Prior Publication Data

US 2022/0071687 A1 Mar. 10, 2022

Related U.S. Application Data

(63) Continuation of application No. PCT/JP2019/022408, filed on Jun. 5, 2019.

(51) Int. Cl.
*A61B 18/02* (2006.01)
*A61B 18/12* (2006.01)
*A61B 18/00* (2006.01)

(52) U.S. Cl.
CPC ...... *A61B 18/1206* (2013.01); *A61B 18/0206* (2013.01); *A61B 2018/00059* (2013.01);
(Continued)

(58) Field of Classification Search
CPC ............... A61B 17/16; A61B 17/1622; A61B 17/1626; A61B 17/1628; A61B 17/32;
(Continued)

(56) References Cited

U.S. PATENT DOCUMENTS 5,157,603 A * 10/1992 Scheller ............... A61B 17/32
606/4
7,905,839 B2 * 3/2011 Misono ............... G01S 15/894
600/459
(Continued)

FOREIGN PATENT DOCUMENTS

CN 110753524 A * 2/2020 ..... A61B 17/320068
CN 108289704 B * 4/2021 ..... A61B 17/320092
(Continued)

OTHER PUBLICATIONS

Dec. 8, 2023 Office Action issued in Korean Patent Application No. 10-2021-7037787.
(Continued)

*Primary Examiner* — Eric S Gibson
(74) *Attorney, Agent, or Firm* — Oliff PLC

(57) ABSTRACT

A drive device includes: a drive signal generator configured to generate a pair of drive signals, a pair of buffer circuits, a pair of switching elements configured to repeatedly turn on and off the pair of drive signals, a first radiation material that has a longitudinal axis and that is arranged to face one of the pair of switching elements, a second radiation material that has a longitudinal axis and that is arranged to face an other one of the pair of switching elements, a fan and a casing. The switching elements, the first radiation material, and the second radiation material are positioned within a projection plane of the fan viewed along the longitudinal axes of the first radiation material and the second radiation material.

14 Claims, 12 Drawing Sheets

(52) U.S. Cl.
CPC ............... *A61B 2018/00178* (2013.01); *A61B 2018/00351* (2013.01); *A61B 2018/0063* (2013.01); *A61B 2018/00916* (2013.01); *A61B 2018/0256* (2013.01)

(58) Field of Classification Search
CPC ........... A61B 17/320068; A61B 2017/320069; A61B 2017/320072; A61B 2017/320073; A61B 2017/320074; A61B 2017/320075; A61B 2017/320077; A61B 2017/320078; A61B 2017/320082; A61B 18/0206; A61B 18/1206; A61B 2018/00178; A61B 2018/00916
See application file for complete search history.

(56) References Cited

U.S. PATENT DOCUMENTS

| | | | | |
|---|---|---|---|---|
| 2002/0141161 | A1* | 10/2002 | Matsukura | H01L 23/42 257/E23.087 |
| 2008/0009744 | A1* | 1/2008 | Misono | G01S 7/52025 600/437 |
| 2012/0097664 | A1 | 4/2012 | Kataoka et al. | |
| 2016/0089537 | A1 | 3/2016 | Yamazaki | |
| 2022/0071687 | A1* | 3/2022 | Nakamura | H05K 7/20 |
| 2022/0318179 | A1* | 10/2022 | Morgan | H02H 9/02 |

FOREIGN PATENT DOCUMENTS

| | | | | |
|---|---|---|---|---|
| CN | 113950297 | A * | 1/2022 | ......... A61B 17/1626 |
| CN | 113950297 | B * | 5/2024 | ......... A61B 17/1626 |
| EP | 3981343 | A1 * | 4/2022 | ......... A61B 17/1626 |
| JP | H09-135843 | A | 5/1997 | |
| JP | 2002-270358 | A | 9/2002 | |
| JP | 2005-034241 | A | 2/2005 | |
| JP | 2006-210516 | A | 8/2006 | |
| JP | 2008-198928 | A | 8/2008 | |
| JP | 2016-40995 | A | 3/2016 | |
| JP | 2017-148538 | A | 8/2017 | |
| JP | 6481029 | B2 * | 3/2019 | ......... A61B 18/1206 |
| WO | 2006/062042 | A1 | 6/2006 | |
| WO | 2011/001568 | A1 | 1/2011 | |
| WO | 2014/196195 | A1 | 12/2014 | |
| WO | 2017/007269 | A1 | 1/2017 | |
| WO | WO-2020245959 | A1 * | 12/2020 | ......... A61B 17/1626 |
| WO | WO-2022208286 | A1 * | 10/2022 | ..... A61B 17/320068 |

OTHER PUBLICATIONS

Jul. 16, 2019 Search Report issued in International Patent Application No. PCT/JP2019/022408.
Nov. 22, 2022 Extended European Search Report issued in European Patent Application No. 19932123.3.
Feb. 28, 2023 Office Action issued in Japanese Patent Application No. 2021-524582.

* cited by examiner

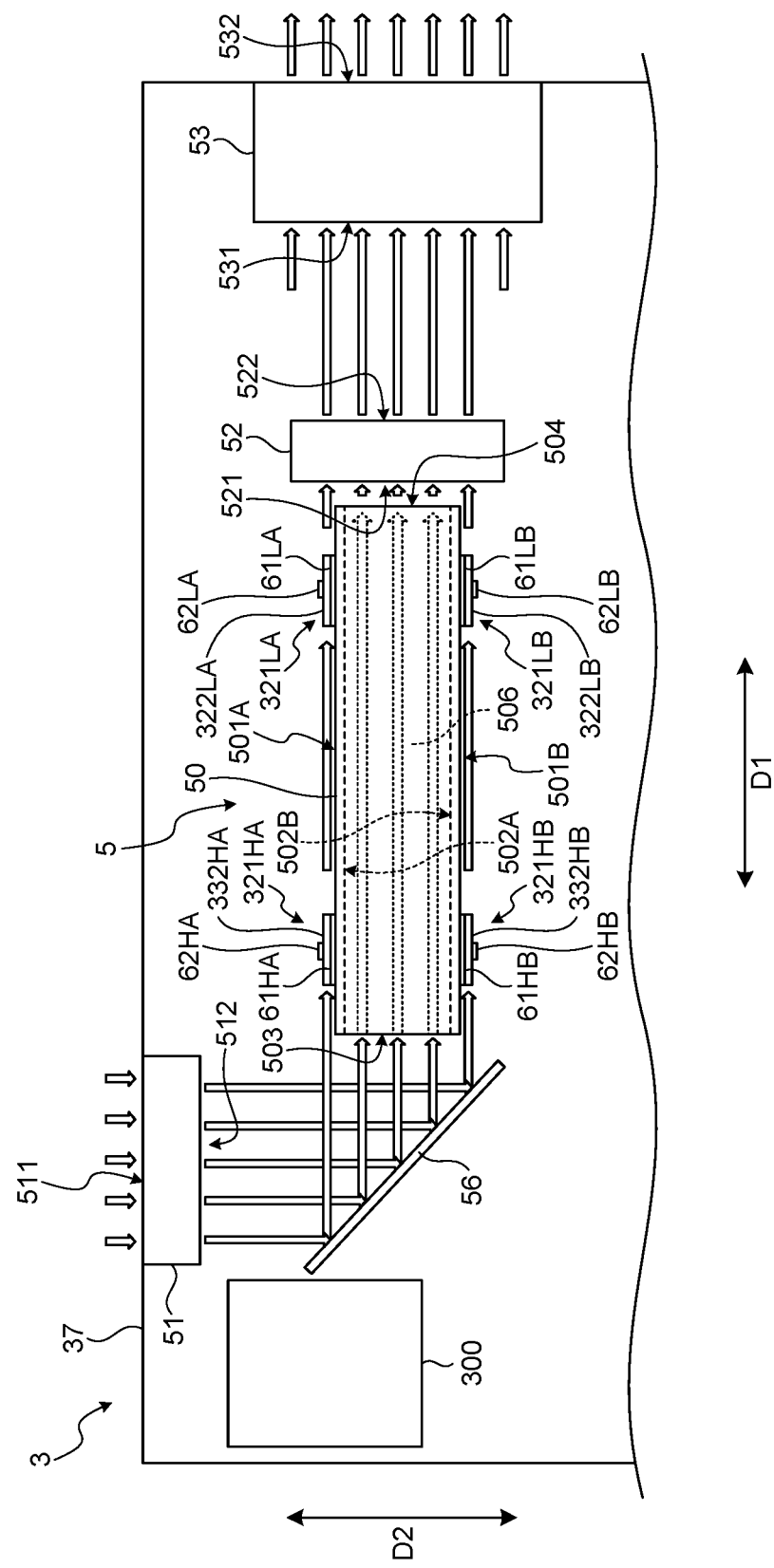

DRIVE DEVICE

CROSS-REFERENCE TO RELATED APPLICATION

This application is a continuation of International Application No. PCT/JP2019/022408, filed on Jun. 5, 2019, the entire contents of which are incorporated herein by reference.

BACKGROUND

1. Technical Field

The present disclosure relates to a drive device that drives a high-frequency treatment tool that is electrically connected to the drive device.

2. Related Art

An ultrasound treatment tool that treats living tissue, for example, inosculates and seals a blood vessel, using ultrasound vibrations that are generated by an ultrasound transducer, has been known as a high-frequency treatment tool (for example, Japanese Laid-open Patent Publication No. 09-135843).

SUMMARY

In some embodiments, a drive device includes: a drive signal generator configured to generate a pair of drive signals for driving a high-frequency treatment tool that is electrically connected to the drive signal generator; a pair of buffer circuits each configured to input respective ones of the pair of drive signals; a pair of switching elements configured to repeatedly turn on and off the pair of drive signals that are output from the pair of buffer circuits at a drive frequency for driving the high-frequency treatment tool or higher; a first radiation material that has a longitudinal axis and that is arranged to face one of the pair of switching elements; a second radiation material that has a longitudinal axis and that is arranged to face an other one of the pair of switching elements; a fan configured to generate an airflow; and a casing configured to house the drive signal generator, the pair of switching elements, the first radiation material, the second radiation material, and the fan. The pair of switching elements, the first radiation material, and the second radiation material are positioned within a projection plane of the fan viewed along the longitudinal axes of the first radiation material and the second radiation material.

In some embodiments, a drive device includes: a drive signal generator configured to generate a pair of drive signals for driving a high-frequency treatment tool that is electrically connected to the drive signal generator; a pair of buffer circuits each configured to input respective ones of the pair of drive signals; a pair of switching elements configured to repeatedly turn on and off the pair of drive signals that are output from the pair of buffer circuits at a drive frequency for driving the high-frequency treatment tool or higher; a first radiation material that has a longitudinal axis and that is arranged to face the pair of switching elements; a fan configured to generate an airflow; and a casing configured to house the drive signal generator, the pair of switching elements, the first radiation material, and the fan. The pair of switching elements and the first radiation material are positioned within a projection plane of the fan viewed along the longitudinal axis of the first radiation material, the first radiation material is cylindrical, the first radiation material includes a first opening that is formed on a side of a first end of the longitudinal axis of the first radiation material; a second opening that is formed on a side of a second end that is an other end of the longitudinal axis of the first radiation material; and a passage communicating between the first opening and the second opening, one of the pair of switching elements is arranged such that the one switching element faces an outer circumferential surface of the first radiation material, and the one switching element and an other of the pair of switching elements face each other in a direction orthogonal to the longitudinal axis with the first radiation material interposed in between.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 14 is a plane view schematically illustrating a configuration of a cooling device that is arranged in a drive device according to a fourth embodiment.

DETAILED DESCRIPTION

First Embodiment

A first embodiment of a drive device according to the disclosure will be described below. Note that the embodiment does not limit the disclosure.

Figure 1:
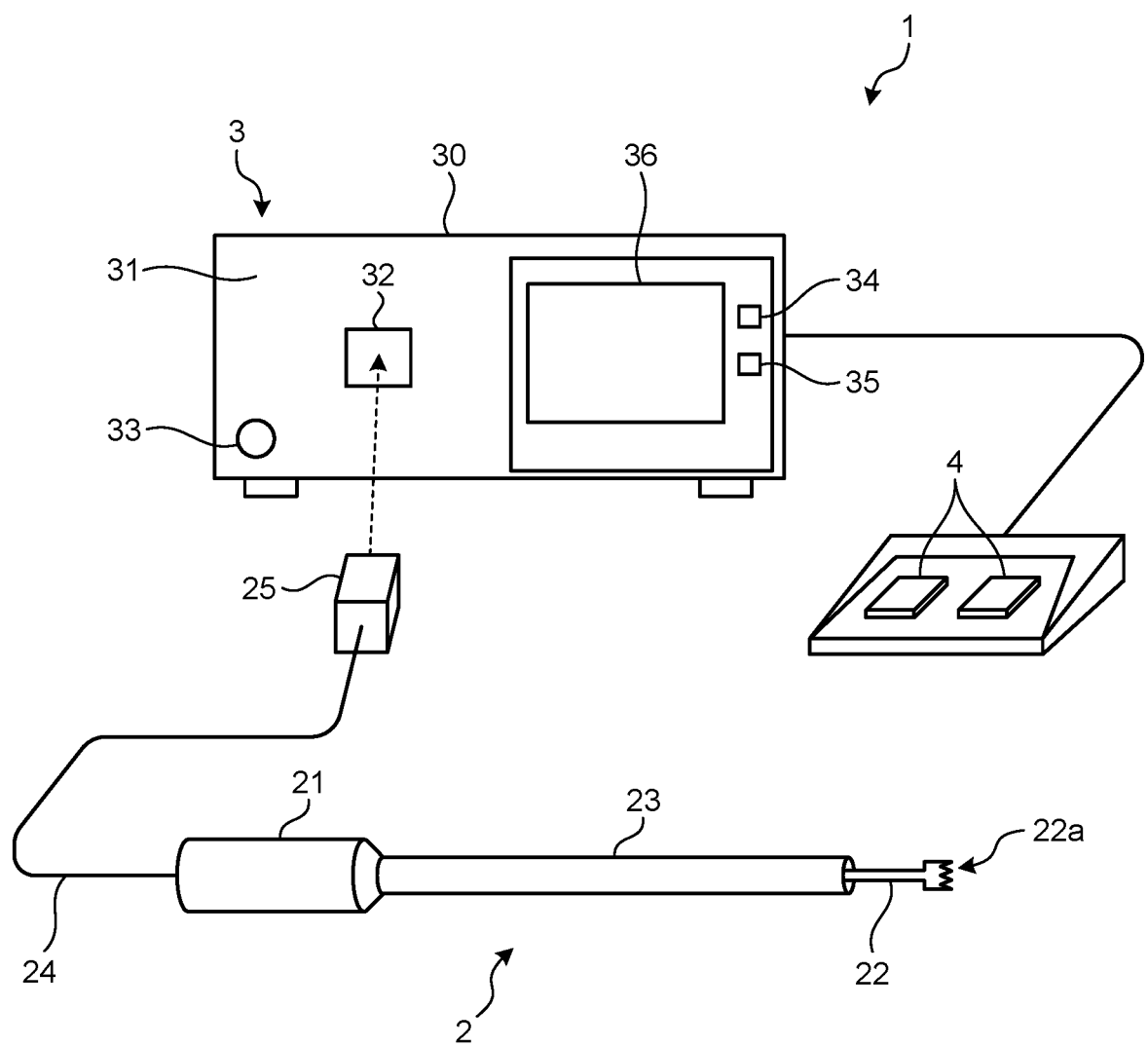
FIG. 1 is a diagram illustrating a schematic configuration of an ultrasound device system according to a first embodiment.

FIG. 1 is a diagram illustrating a schematic configuration of an ultrasound device system according to the first embodiment. As illustrated in FIG. 1, an ultrasound device system 1 according to the first embodiment includes an ultrasound treatment tool 2 that is an ultrasound device, a drive device 3 for driving the ultrasound treatment tool 2, and a foot switch 4 for issuing an instruction for turning on or off ultrasound vibrations of the ultrasound treatment tool 2.

The ultrasound treatment tool 2 is configured by including a treatment tool body 21, a probe 22, a sheath 23, a cable 24, a connector 25, etc. The treatment tool body 21 is cylindrical and houses an ultrasound transducer consisting of piezoelectric member for which lead zirconate titanate (PZT) is used, a drive energy input unit that is for driving the ultrasound transducer and that is to be described below, etc. A proximal end of the probe 22 is connected to the treatment tool body 21. A treatment unit 22a is arranged at a distal end of the probe 22. The sheath 23 is cylindrical and that is elongated more than the treatment tool body 21 and covers part of an outer circumference of the probe 22 from the treatment tool body 21 by a given length. A proximal end of the cable 24 is electrically connected to the drive energy input unit, etc., in the treatment tool body 21. The connector 25 is connected to the distal end of the cable 24.

The drive device 3 includes a casing 30 that is cuboid and houses, in the casing 30, multiple electric parts of which an electric circuit, etc., consist, etc. In the casing 30, in the state where the drive device 3 is placed on a setting plane and in a posture such that the drive device 3 is usable, a front panel 31 is arranged on a single plane that erects on the setting plane. On the front panel 31, as illustrated in FIG. 1, a connector 32, a power switch 33, two operation switches 34 and 35, a display screen 36, etc., are arranged. The connector 25 of the cable 24 of the ultrasound treatment tool 2 is detachably connected to the connector 32. The connector 25 and the connector 32 are connected and thus drive power is supplied and control signals are communicated between the connector 25 and the connector 32 via the cable 24.

In the ultrasound device system 1 according to the first embodiment, a practitioner operates the foot switch 4 by foot and thereby drive power from the drive device 3 causes the ultrasound transducer of the ultrasound treatment tool 2 to generate ultrasound vibrations and thus the treatment unit 22a of the probe 22 is able to perform bone cutting treatment.

Figure 2:
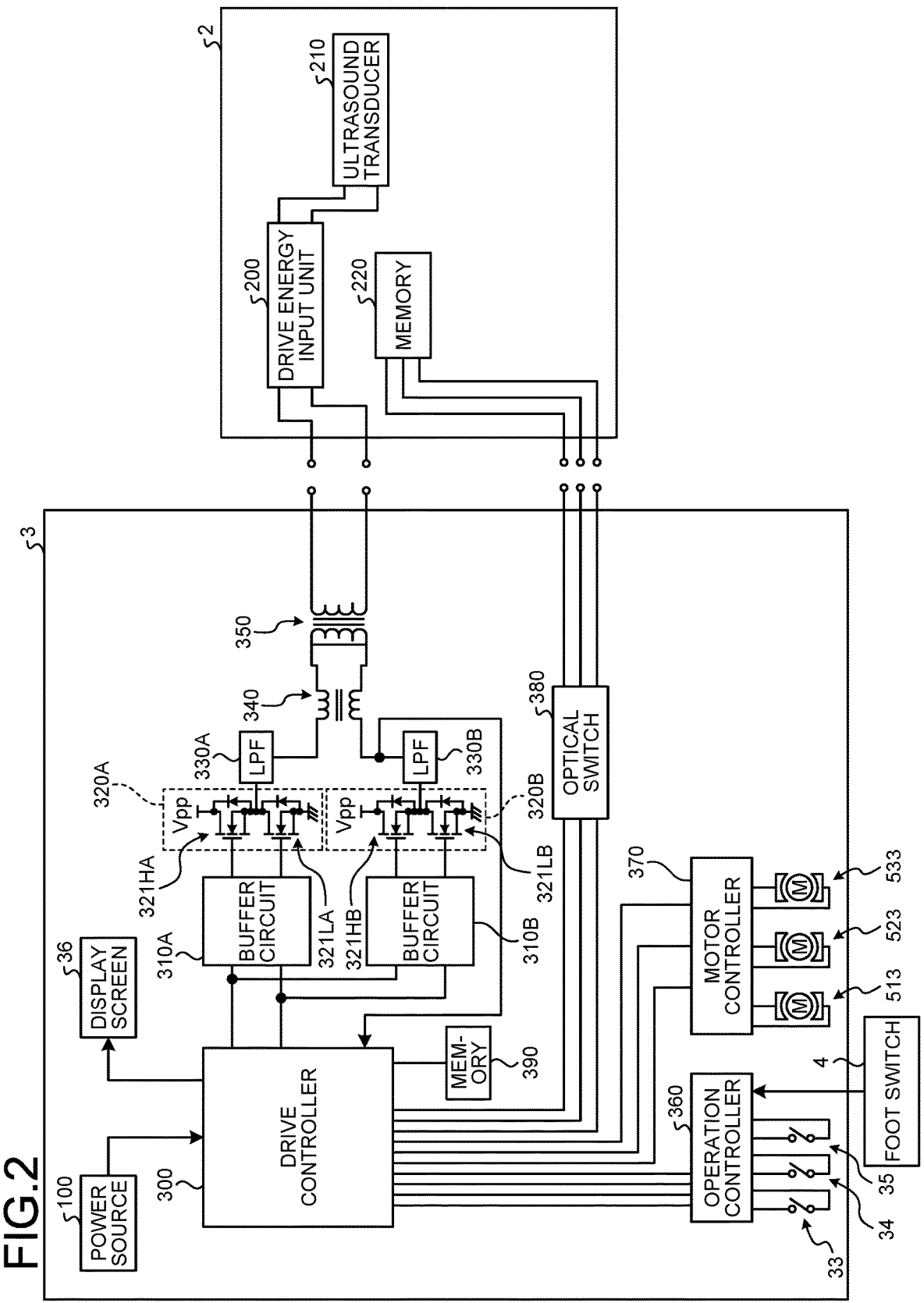
FIG. 2 is a block diagram illustrating a circuit configuration of an ultrasound treatment tool and a drive device according to the first embodiment.

FIG. 2 is a block diagram illustrating a circuit configuration of the ultrasound treatment tool 2 and the drive device 3 according to the first embodiment. In FIG. 2, the ultrasound treatment tool 2 includes a drive energy input unit 200, an ultrasound transducer 210, and a memory 220. The drive device 3 includes a drive controller 300, buffer circuits 310A and 310B, switching circuits 320A and 320B, low-pass filters 330A and 330B, a common mode coil 340, an output transformer 350, an operation controller 360, a motor controller 370, an optical switch 380, and a memory 390.

Operations of the drive device 3 configured as described above will be described. A user presses the power switch 33 and a signal from the operation controller 360 is input and then the drive controller 300 to which power is supplied from the power source 100 functions as, for example, a drive signal generator that generates drive signals for driving the ultrasound treatment tool 2 and outputs drive signals respectively to the buffer circuits 310A and 310B in a pair.

The buffer circuits 310A and 310B reduce a load on the drive controller 300 and make outputs to the switching circuits 320A and 320B in a pair. The route via the buffer circuits 310A and 310B makes it possible to increase switching efficiency.

In the switching circuit 320A, a high side switching element 321HA and a low side switching element 321LA are arranged. In the switching circuit 320B, a high side witching element 321HB and a low side switching element 321LB are arranged. In the following description, when the four switching elements 321HA, 321HB, 321LA, and 321LB are not particularly distinguished from one another, they are simply referred to as switching elements 321. For example, a field-effect transistor (FET), or the like, is usable as the switching element 321.

In the switching circuits 320A and 320B, based on the drive signals that are output from the buffer circuits 310A and 310B, the high side switching elements 321HA and 321HB and the low side switching elements 321LA and 321LB are alternately turned on and off at a frequency equal to or higher than a drive frequency of the ultrasound transducer.

The outputs of the switching circuits 320A and 320B are input to a primary side of the output transformer 350 respectively via the low-pass filters 330A and 330B and the common mode coil 340. The outputs of the switching circuits 320A and 320B pass through the low-pass filters 330A and 330B and thus are converted into drive signals having sine waves for driving the ultrasound transducer ("ultrasound drive signals" below).

In the drive device 3 according to the first embodiment, increasing the outputs increase noise and noise contained in the ultrasound drive signals is reduced by mounting the common mode coil 340 between the low-pass filters 330A and 330B and the output transformer 350.

The ultrasound drive signals having some waves are input to the primary side of the output transformer 350 and thus the ultrasound drive signals that are boosted more than those to the primary side of the output transformer 350 are output to a secondary side of the output transformer 350. The ultrasound drive signals that are output to the secondary side of the output transformer 350 are output to the drive energy input unit 200 of the ultrasound treatment tool 2 and the drive energy input unit 200 causes the ultrasound transducer 210 to cause ultrasound vibration.

The drive controller 300 connects to the memory 220 of the ultrasound treatment tool 2 via the optical switch 380 and determines the type of the ultrasound treatment tool 2, etc., by reading ID information on the ultrasound treatment tool 2 that is stored in the memory 220. Based on information that is stored in the memory 390, the drive controller 300 sets drive parameters (a base frequency, a current value, a maximum successive output time, etc.) according to the determined type of the ultrasound treatment tool 2. The drive controller 300 generates drive signals based on a feedback result of the voltage and current of the ultrasound drive signals.

In the drive device 3 according to the first embodiment, the magnitude of the ultrasound drive signals that are output to the ultrasound treatment tool 2 from the drive device 3 are displayed on the display screen 36. The magnitudes of the ultrasound drive signals that are output to the ultrasound treatment tool 2 from the drive device 3 are adjustable based on signals that are output from the operation controller 360 because the foot switch 4 and the operation switches 34 and 35 are operated.

In the drive device 3 according to the first embodiment, in order to deal with increased output of the ultrasound drive signals, the rating of the switching elements 321HA, 321HB, 321LA and 321LB of the switching circuits 320A and 320B is set higher than that of a switching element of a drive device for driving an ultrasound treatment tool that treats a blood vessel and that is different from the ultrasound treatment tool 2 of the first embodiment. For this reason, in the configuration in which drive signals are output from the drive controller 300 directly to the switching circuits 320A and 320B, it is necessary to output drive signals of high output from the drive controller 300 and this increases a load on the drive controller 300 and the amount of heat generated by the drive controller 300 increases.

On the other hand, in the drive device 3 according to the first embodiment, the buffer circuits 310A and 310B are arranged between the drive controller 300 and the switching circuits 320A and 320B and drive signals from the drive controller 300 are output to the buffer circuits 310A and 310B and then are output to the switching circuits 320A and 320B. Thus, drive signals of lower output than in the configuration in which drive signals are output directly from the drive controller 300 to the switching circuits 320A and 320B may be output from the drive controller 300 and this makes it possible to lower the load on the drive controller 300. Thus, the drive device 3 according to the first embodiment makes it possible to realize ultrasound drive signals of high output while reducing the amount of heat generated by the drive controller 300.

The drive device 3 according to the first embodiment includes a cooling device 5 as a countermeasure against heat generation in order to cool the switching elements 321HA, 321HB, 321LA and 321LB. The cooling device 5 will be described below.

Figure 3:
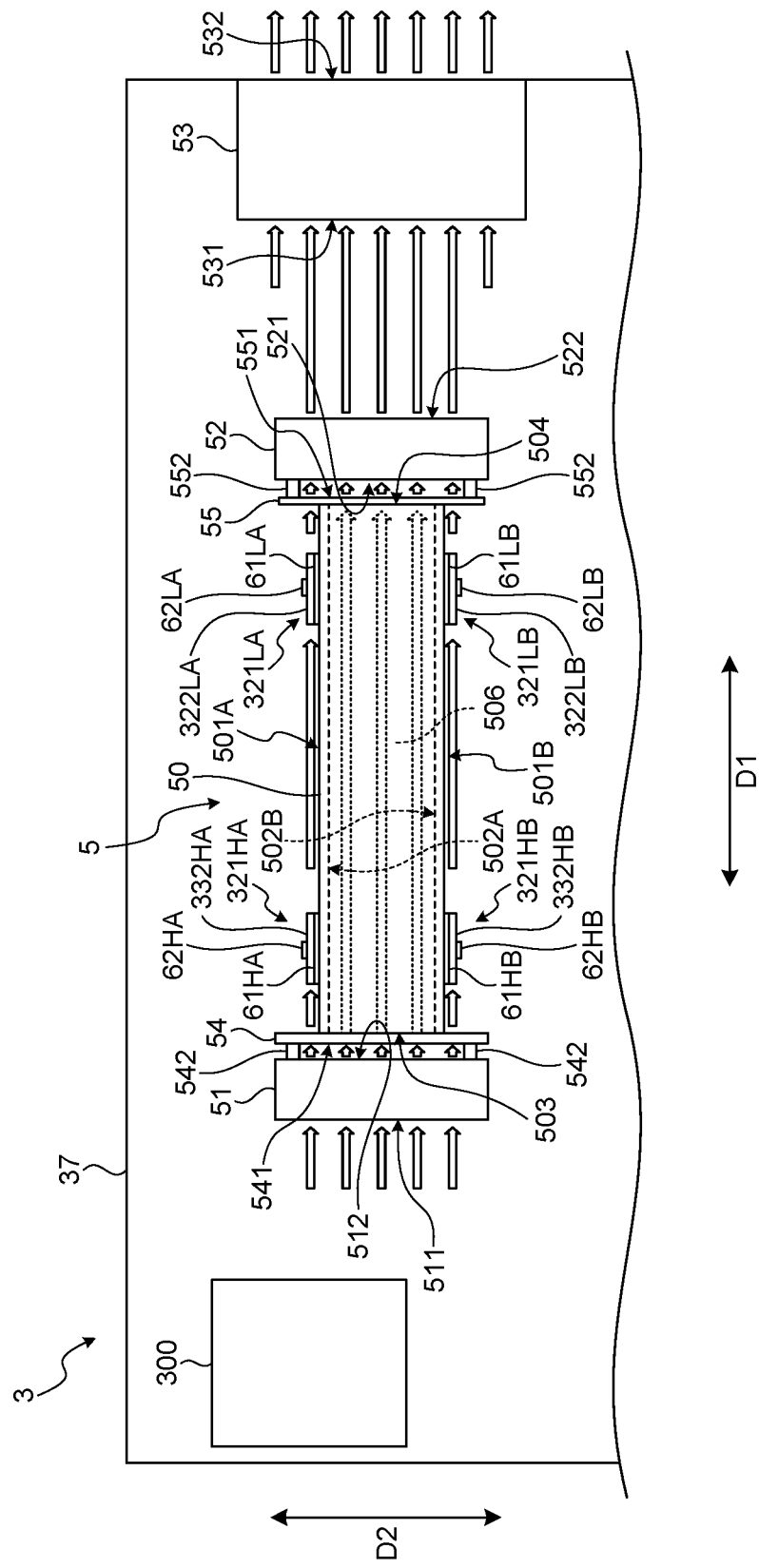
FIG. 3 is a plane view schematically illustrating a configuration of a cooling device that is arranged in the drive device according to the first embodiment.

FIG. 3 is a plane view schematically illustrating a configuration of the cooling device 5 that is mounted on the drive device 3 according to the first embodiment.

In FIG. 3, the configuration of the cooling device 5 will be described. The cooling device 5 includes a single heatsink 50, a first cooling fan 51, a second cooling fan 52, and a discharge fan 53. The heatsink 50 is cuboid, has a longitudinal axis, and is formed using aluminum, aluminum alloy, copper, a copper alloy, or the like. A grounding wire not illustrated in the drawing is connected to the heatsink 50 in a position for which assembling easiness and thermal effects are taken into consideration. The first cooling fan 51, the second cooling fan 52, and the discharge fan 53 are axial current fans, respectively have inlets 511, 521 and 531 and outlets 512, 522 and 532, and are arranged such that their rotation axis lines are positioned on the same straight line.

The switching elements 321HA and 321LA of the switching circuit 320A face an outer surface 501A that is an outer circumferential surface of the heatsink 50. An element body 322HA of the switching element 321HA and an element body 322LA of the switching element 321LA are fixed to the outer surface 501A by screws 62HA and 62LA respectively via radiating sheets 61HA and 61LA with which the element body 322HA and the element body 322LA are making contact. Note that an inner surface 502A that is an inner circumferential surface of the heatsink 50 is formed on the back side of the outer surface 501A of the heatsink 50.

The switching elements 321HB and 321LB of the switching circuit 320B face an outer surface 501B that is an outer circumferential surface of the heatsink 50. An element body 322HB of the switching element 321HB and an element body 322LB of the switching element 321LB are fixed to the outer surface 501B by screws 62HB and 62LB respectively via radiating sheets 61HB and 61LB with which the element body 322HB and the element body 322LB are making contact. Note that an inner surface 502B that is an inner circumferential surface of the heatsink 50 is formed on the back side of the outer surface 501B of the heatsink 50.

Each of the element bodies 322HA, 322HB, 322LA and 322LB and the screws 62HA, 62HB, 62LA and 62LB are electrically insulated. The radiation sheets 61HA, 61HB, 61LA and 61LB are made of a material, such as silicon rubber, that is insulating, that has high heat conductivity, and that is capable of elastic deformation.

An air inlet 503 serving as a first opening is formed on a side of a first end that is an end of the longitudinal axis of the heatsink 50 and an air outlet 504 that is a second opening is formed on a side of a second end that is the other end of the longitudinal axis of the heatsink 50.

Figure 4:
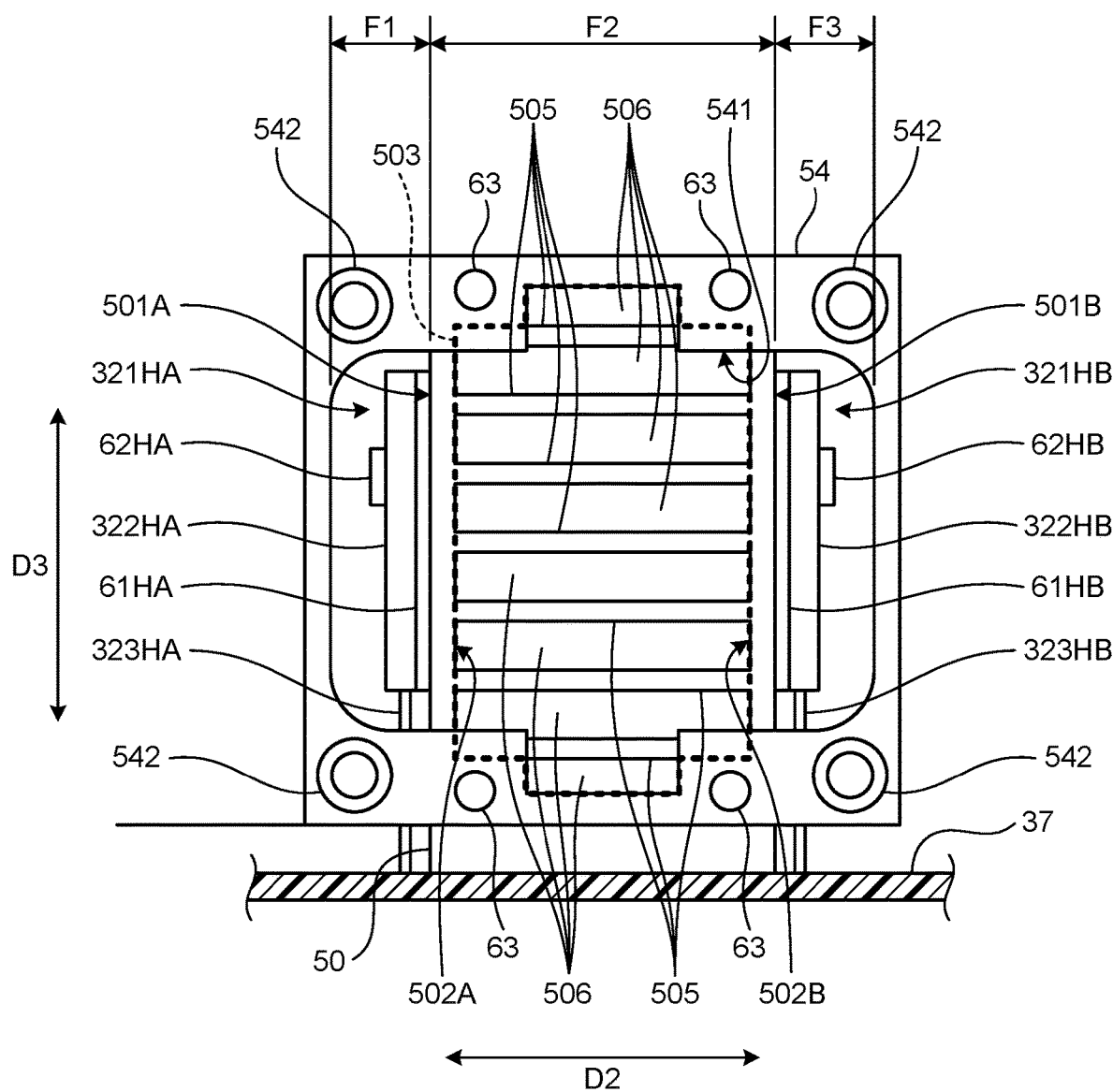
FIG. 4 is a side view of the cooling device viewed from the side of a first cooling fan.

The open arrows in FIG. 3 represent air flows. The arrow D1 in FIG. 3 represents a longitudinal direction that is parallel to the longitudinal axis of the heatsink 50 and the arrow D2 in FIG. 3 represents a heatsink width direction that is orthogonal to the longitudinal direction D1 of the heatsink 50. FIG. 4 is a side view of the cooling device 5 viewed from the side of the first cooling fan 51. Note that illustration of the first cooling fan 51 is omitted in FIG. 4.

In the heatsink 50, ventilation paths 506 that are a plurality of flat paths are formed between the air inlet 503 and the air outlet 504 via a plurality of fins 505 along the longitudinal direction D1 of the heatsink 50. Forming the ventilation paths 506 by arranging the fins 505 in the hollow of the heatsink 50 makes it possible to increase the surface area of the heatsink 50 and thus increases radiation from the heatsink 50 to the air. Note that the fins 505 are not limited to ones that, as illustrated in FIG. 4, extend continuously in the heatsink width direction D2 between the inner surface 502A and the inner surface 502B. For example, the fins may be formed from the inner surface 502A and the inner surface 502B in an erecting manner in the heatsink width direction D2 such that a gap is formed between the tips of the fins.

As illustrated in FIG. 4, a fixation plate 54 that is rectangular and that is a fixation material for fixing the first cooling fan 51 is screwed with four screws 63 to an end face of the heatsink 50 on the side of the first end in the longitudinal direction D1. In the fixation plate 54, an opening 541 larger than the air inlet 503 of the heatsink 50 is formed and also functions as a rectifying member that is arranged between the first cooling fan 51 and the heatsink 50. The opening 541 is open to the outer side in the heatsink width direction D2 relative to the switching elements 321HA and 321HB that are fixed respectively to the outer surface 501A and the outer surface 501B. The opening 541 is open to communicate with all the ventilation paths 506 of the heatsink 50 in a heatsink height direction D3.

The opening 541 can be sectioned in the heatsink width direction D2 into a first area F1 on an outer side relative to the outer surface 501A of the heatsink 50, a second area F2 between the outer surface 501A and the outer surface 501B of the heatsink 50, and a third area F3 on an outer side relative to the outer surface 501B of the heatsink 50. The area of opening in the second area F2 is larger than each of the areas of opening in the first area F1 and the third area F3.

On the four corners of the fixation plate 54, screw holes 542 that are cylindrical and that are for screwing the first cooling fan 51 are formed in positions corresponding to screw through-holes that are not illustrated in the drawing and that are formed on the four corners of the first cooling fan 51. With the outlet 512 being oriented to the side of the air inlet 503 of the heatsink 50, screws are inserted into the screw through-holes and the screw holes 542 and thus the first cooling fan 51 is fixed to the fixation plate 54. As described above, the first cooling fan 51 is fixed to the fixation plate 54 and accordingly the first cooling fan 51 is set in a position being away from the heatsink 50. Accordingly, it is possible to avoid the heatsink 50 and the first cooling fan 51 from making direct contact with each other, allow a wind to easily go out of the space that is formed between the heatsink 50 and the first cooling fan 51, and thus make heat less stagnant.

Figure 5:
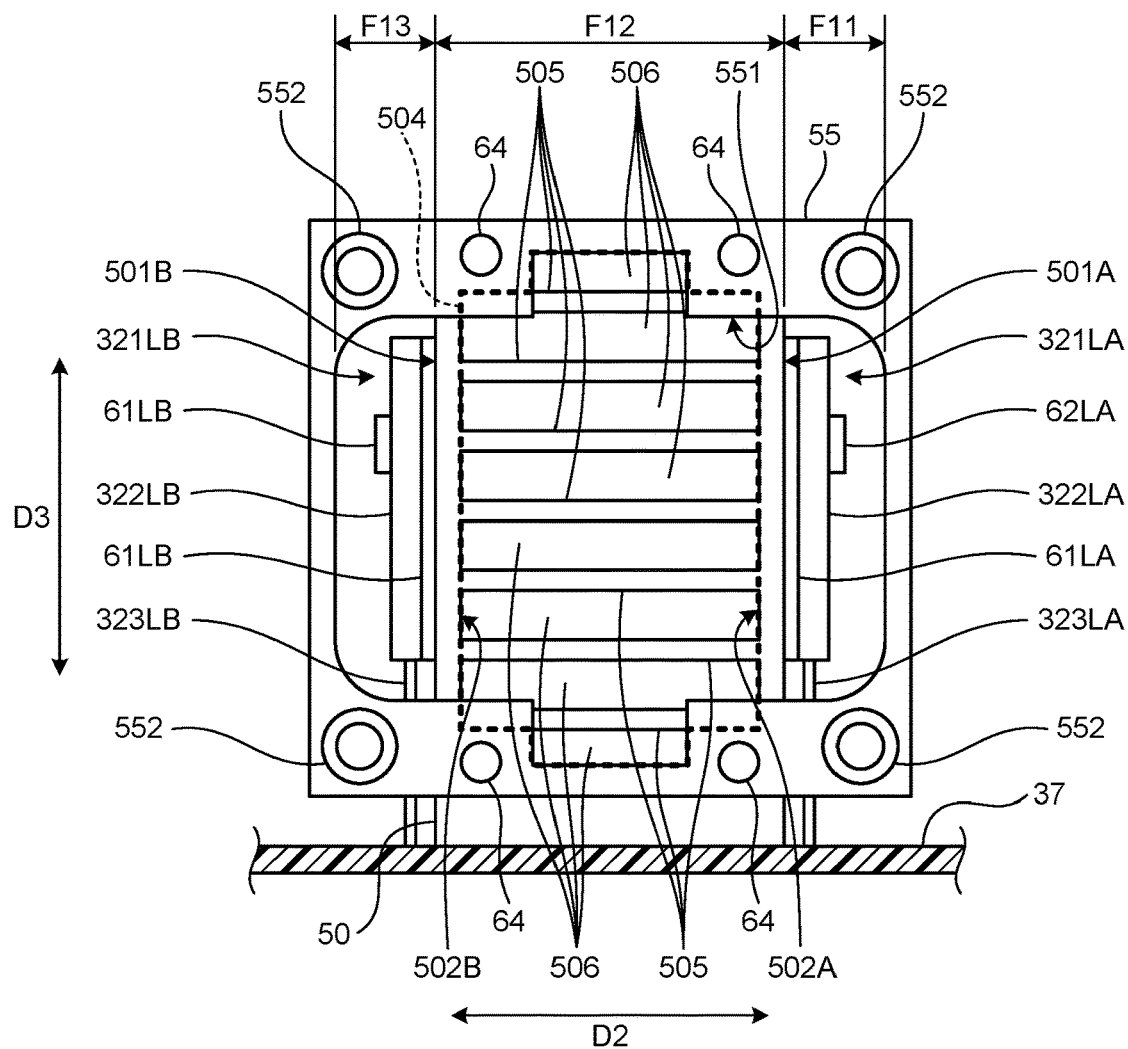
FIG. 5 is a side view of the cooling device viewed from the side of a second cooling fan.

FIG. 5 is a side view of the cooling device 5 viewed from the side of the second cooling fan 52. In FIG. 5, illustration of the second cooling fan 52 is omitted. The arrow D3 in FIG. 4 and FIG. 5 represents a heatsink height direction that is orthogonal to the longitudinal direction D1 and the heatsink width direction D2 of the heatsink 50.

As illustrated in FIG. 5, a fixation plate 55 that is rectangular and that is a fixation material for fixing the second cooling fan 52 that is a drawing fan is screwed with four screws 64 to an end face of the heatsink 50 on the side of the second end in the longitudinal direction D1. In the fixation plate 55, an opening 551 larger than the air outlet 504 of the heatsink 50 is formed and also functions as a rectifying member that is arranged between the second cooling fan 52 and the heatsink 50. The opening 551 is open to the outer side in the heatsink width direction D2 relative to the switching elements 321LA and 321LB that are fixed respectively to the outer surface 501A and the outer surface 501B. The opening 551 is open to communicate with all the ventilation paths 506 of the heatsink 50 in the heatsink height direction D3.

The opening 551 can be sectioned in the heatsink width direction D2 into a first area F11 on an outer side relative to the outer surface 501A of the heatsink 50, a second area F12 between the outer surface 501A and the outer surface 501B of the heatsink 50, and a third area F13 on an outer side relative to the outer surface 501B of the heatsink 50. The area of the opening in the second area F12 is larger than each of the areas of the first area F11 and the third area F13.

On the four corners of the fixation plate 55, screw holes 552 that are cylindrical and that are for screwing the second cooling fan 52 are formed in positions corresponding to screw through-holes that are not illustrated in the drawing and that are formed on the four corners of the second cooling fan 52. With the outlets 522 being oriented to the side of the air outlet 504 of the heatsink 50, screws are inserted into the screw through-holes and the screw holes 552 and thus the second cooling fan 52 is fixed to the fixation plate 55. As described above, the second cooling fan 52 is fixed to the fixation plate 55 and accordingly the second cooling fan 52 is set in a position being away from the heatsink 50. Accordingly, it is possible to avoid the heatsink 50 and the second cooling fan 52 from making direct contact with each other and allow a wind to easily go out of the space that is formed between the heatsink 50 and the second cooling fan 52, which makes heat less stagnant.

As illustrated in FIG. 4 and FIG. 5, connection terminals 323HA, 323HB, 323LA and 323LB that the switching elements 321HA, 321HB, 321LA and 321LB include, respectively, are soldered onto a circuit board 37.

In the cooling device 5 of the first embodiment, the first cooling fan 51 is fixed to the fixation plate 54 that is arranged on the side of the first end of the heatsink 50 in the longitudinal direction D1 and thus the heatsink 50 and the switching elements 321HA, 321HB, 321LA and 321LB are positioned within a projection plane of the first cooling fan 51 viewed along the longitudinal direction D1 (longitudinal axis) of the heatsink 50. Operating the first cooling fan 51 forms an airflow along the outer surface 501A of the heatsink 50, an airflow along the outer surface 501B of the heatsink 50, and airflows along the ventilation paths 506 of the heatsink 50. Accordingly, the heat of the heatsink 50 is radiated to the air flowing along the outer surface 501A and air flowing along the ventilation paths 506. This promotes heat radiation from the switching elements 321HA, 321HB, 321LA and 321LB to the heatsink 50 and cools the switching elements 321HA, 321HB, 321LA and 321LB.

In the cooling device 5 of the first embodiment, the airflow along the outer surface 501A to which the switching elements 321HA and 321LA are fixed and the airflow along the inner surface 502A on the back side of the outer surface 501A are formed simultaneously. For this reason, it is possible to radiate the heat that is radiated from the switching elements 321HA and 321LA to the heatsink 50 to the air efficiently more than when an airflow along only any one of the outer surface 501A and the inner surface 502A is formed.

In the cooling device 5 of the first embodiment, an airflow along the outer surface 501B to which the switching elements 321HB and 321LB are fixed and an airflow along the inner surface 502B on the back side of the outer surface 501B are formed simultaneously. For this reason, it is possible to radiate the heat that is radiated from the switching elements 321HB and 321LB to the heatsink 50 to the air efficiently more than when an airflow along only any one of the outer surface 501B and the inner surface 502B is formed.

In the cooling device 5 of the first embodiment, because the airflows along the outer surfaces 501A and 501B and the inner surfaces 502A and 502B are generated by the common first cooling fan 51, it is possible to reduce the size of the cooling device 5 and eventually reduce the size of the drive device 3.

Furthermore, in the cooling device 5 of the first embodiment, the airflow along the outer surface 501A and the airflow along the outer surface 501B hit the switching elements 321HA, 321HB, 321LA and 321LB, respectively. This makes it possible to promote not only radiation from the switching elements 321HA, 321HB, 321LA and 321LB to the heatsink 50 but also radiation from the switching elements 321HA, 321HB, 321LA and 321LB to the air and thus cool the switching elements 321HB and 321LB more efficiently.

As described above, in the drive device 3 according to the first embodiment, the cooling device 5 cools the heatsink 50 and the switching elements 321, thereby making it possible to inhibit the temperature of the switching elements 321 from increasing and thus inhibit the switching element 321 from being at or more than a rated temperature. Accordingly, in the drive device 3 according to the first embodiment, when driving the ultrasound treatment tool 2 by drive energy of a high output, it is possible to inhibit the temperature of the drive device 3 from increasing due to a loss in the element.

In the cooling device 5 of the first embodiment, the second cooling fan 52 is fixed to the fixation plate 55 that is arranged on the side of the second end of the heatsink 50 in the longitudinal direction D1 and thus the heatsink 50 and the four switching elements 321HA, 321HB, 321LA and 321LB are positioned within a projection plane of the second cooling fan 52 viewed along the longitudinal direction D1 (longitudinal axis) of the heatsink 50. Operating the second cooling fan 52 causes the airflows that are formed by the first cooling fan 51 and that reach the side of the second end of the heatsink 50 in the longitudinal direction D1 along the outer surface 501A and the outer surface 501B of the heatsink 50 and the airflows that go out of the air outlet 504 of the heatsink 50 are drawn from the inlet 521 of the second cooling fan 52 via the opening 551 of the fixation plate 55.

Thus, the air that is radiated from the heatsink 50 and the switching elements 321 is inhibited from stagnating on the side of the second end of the heatsink 50 in the longitudinal direction D1, which enables efficient discharge.

The discharge fan 53 is arranged in an exhaust opening that is not illustrated in the drawing and that is formed in the casing 30 of the drive device 3 and through which the inside and the outside of the casing 30 communicate. The heatsink 50 and the switching elements 321HA, 321HB, 321LA and 321LB are positioned within a projection plane of the discharge fan 53 viewed along the longitudinal direction D1 of the heatsink 50. The radiated air that is drawn from the inlet 521 of the second cooling fan 52 goes out of the outlet 522 of the second cooling fan 52. The radiated air is drawn from the inlet 531 of the discharge fan 53 and is discharged from the outlet 532 of the discharge fan 53 to the outside of the casing 30 via the exhaust opening.

In the drive device 3 according to the first embodiment, the switching element 321HA that is fixed to the outer surface 501A of the heatsink 50 and the switching element 321HB that is fixed to the outer surface 501B of the heatsink 50 face each other in the heatsink width direction D2 with the heatsink 50 being interposed in between. The switching element 321LA that is fixed to the outer surface 501A of the heatsink 50 and the switching element 321LB that is fixed to the outer surface 501B of the heatsink 50 face each other in the heatsink width direction D2 with the heatsink 50 interposed in between. This makes it possible to, while keeping the circuit balance between the switching circuit 320A and the switching circuit 320B, radiate heat from the four switching elements 321HA, 321HB, 321LA, and 321LB to the air and reduce the size of the drive device 3.

Figure 6:
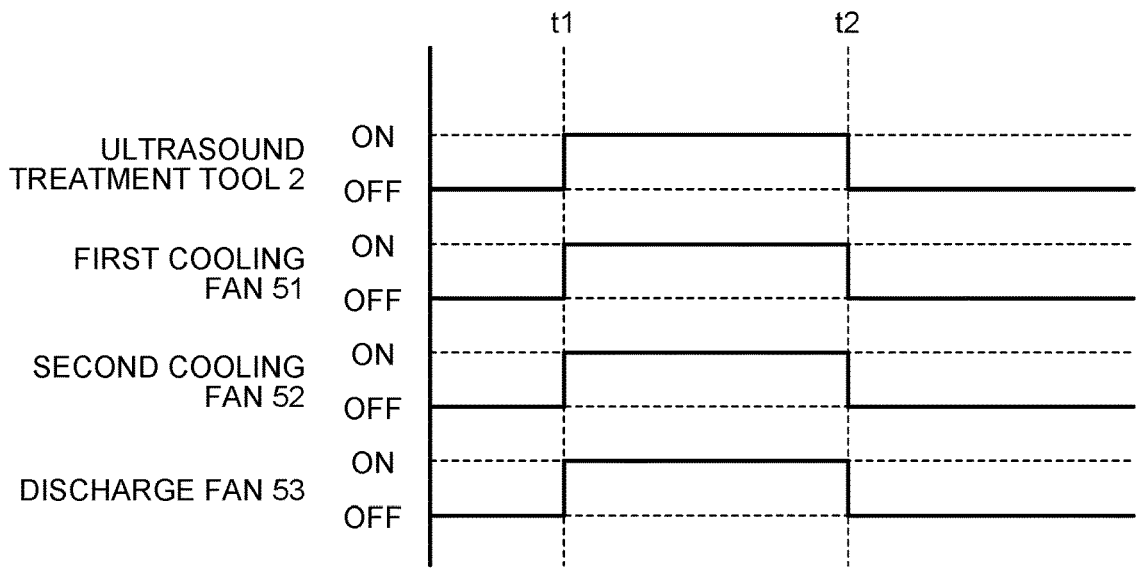
FIG. 6 is a timing chart illustrating a first example of on-off control on the ultrasound treatment tool, the first cooling fan, the second cooling fan, and a discharge fan.

FIG. 6 is a timing chart illustrating a first example of on-off control on the ultrasound treatment tool 2, the first cooling fan 51, the second cooling fan 52, and the discharge fan 53.

In the on-off control illustrated in FIG. 6, the first cooling fan 51, the second cooling fan 52 and the discharge fan 53 are caused to operate synchronously during operation of the ultrasound treatment tool 2. In other words, as illustrated in FIG. 6, at time t1, the drive controller 300 switches the ultrasound treatment tool 2, the first cooling fan 51, the second cooling fan 52, and the discharge fan 53 on from off to cause them to start operations simultaneously. Thereafter, at time t2 after elapse of a given time, the drive controller 300 switches the ultrasound treatment tool 2, the first cooling fan 51, the second cooling fan 52, and the discharge fan 53 off from on to cause them to stop their respective operations.

In the on-off control illustrated in FIG. 6, causing the first cooling fan 51, the second cooling fan 52 and the discharge fan 53 to operate synchronously during operation of the ultrasound treatment tool 2 makes it possible to promote radiation of the heatsink 50 and the switching elements 321 and thus ensure high cooling performance.

Figure 7:
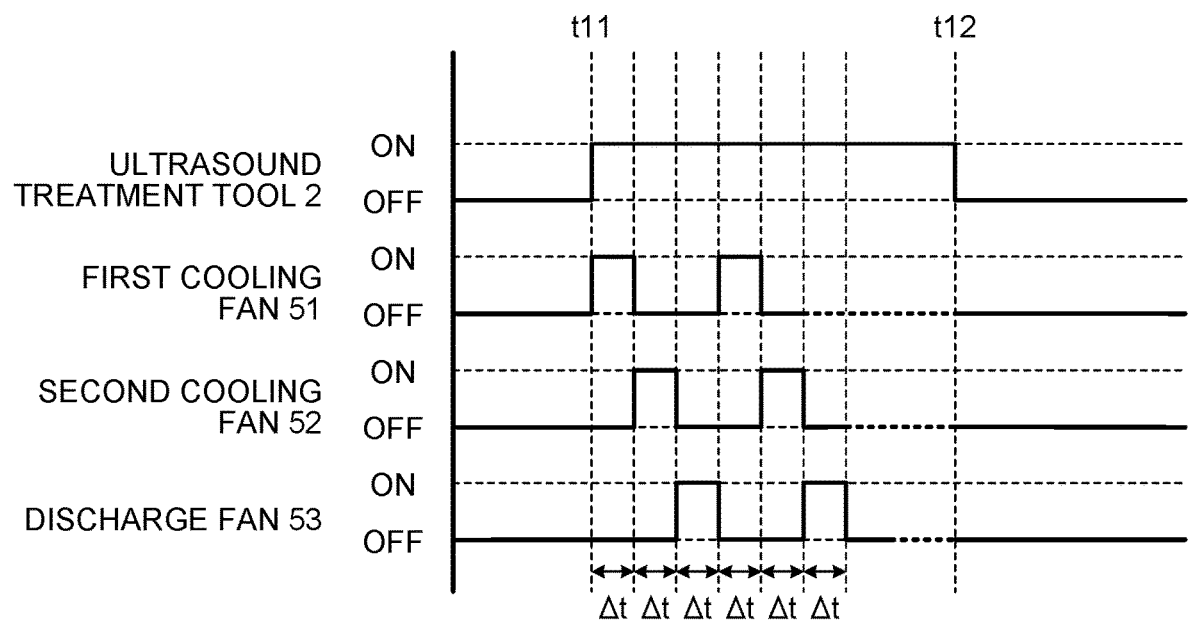
FIG. 7 is a timing chart illustrating a second example of on-off control on the ultrasound treatment tool, the first cooling fan, the second cooling fan, and the discharge fan.

FIG. 7 is a timing chart illustrating a second example of the on-off control on the ultrasound treatment tool 2, the first cooling fan 51, the second cooling fan 52 and the discharge fan 53.

In the on-off control illustrated in FIG. 7, each of the first cooling fan 51, the second cooling fan 52 and the discharge fan 53 is caused to perform operation intermittently by shifting the timing of each of the fans by time Δt. In other words, as illustrated in FIG. 7, at time t11, the drive controller 300 switches the ultrasound treatment tool 2 on from off to cause the ultrasound treatment tool 2 to start the operation and switches the first cooling fan 51 on from off to cause the first cooling fan 51 to start the operation. After causing the first cooling fan 51 to operate for only time Δt, the drive controller 300 switches the first cooling fan 51 off from on and switches the second cooling fan 52 on from off. After causing the second cooling fan 52 to operate for only time Δt, the drive controller 300 switches the second cooling fan 52 off from on and switches the discharge fan 53 on from off. After causing the discharge fan 53 to operate for only time Δt, the drive controller 300 switches the discharge fan 53 off from on and switches the first cooling fan 51 on from off. Thereafter, the drive controller 300 causes each of the first cooling fan 51, the second cooling fan 52 and the discharge fan 53 operate for time Δt intermittently by shifting the timing of each of the fans until the ultrasound treatment tool 2 is caused to stop the operation. Thereafter, the drive controller 300 turns the ultrasound treatment tool 2 off from on to stop the operation and turns any one of the first cooling fan 51, the second cooling fan 52 and the discharge fan 53 that is operating at that time off from on to stop the operation.

The first cooling fan 51, the second cooling fan 52 and the discharge fan 53 are axial current fans and thus rotate because of inertia also after being switched off from on. For this reason, in the on-off control illustrated in FIG. 7, causing each of the first cooling fan 51, the second cooling fan 52 and the discharge fan 53 to operate intermittently by shifting the timing of each of the fans during the operation of the ultrasound treatment tool 2 makes it possible to ensure cooling performance and reduce power consumption.

Figure 8:
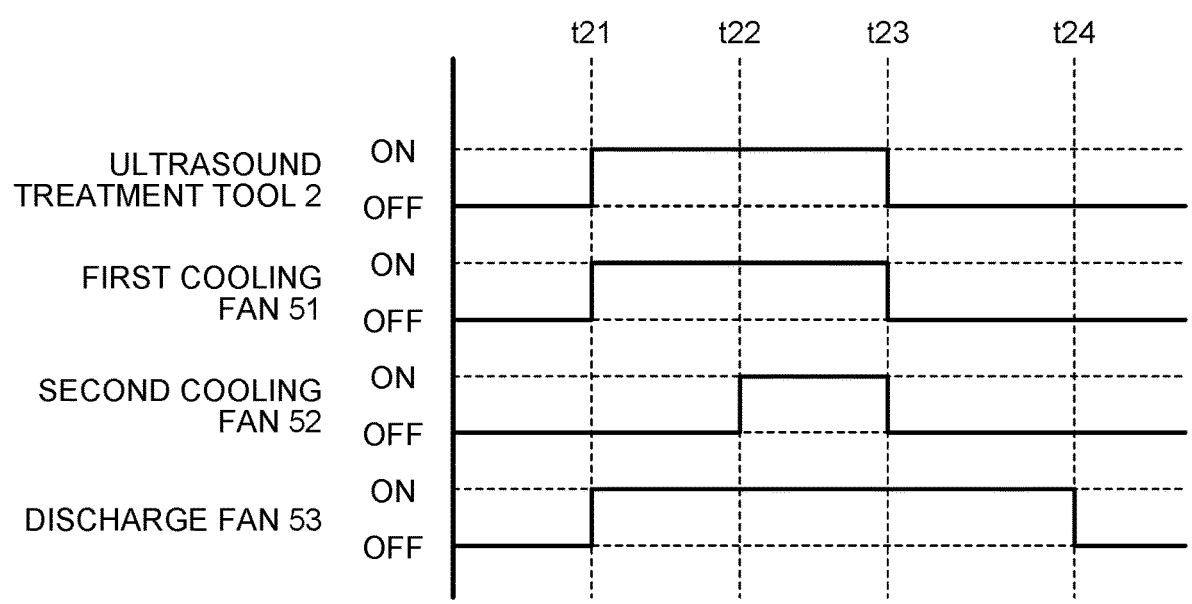
FIG. 8 is a timing chart illustrating a third example of on-off control on the ultrasound treatment tool, the first cooling fan, the second cooling fan, and the discharge fan.

FIG. 8 is a timing chart illustrating a third example of on-off control on the ultrasound treatment tool 2, the first cooling fan 51, the second cooling fan 52 and the discharge fan 53.

In the on-off control illustrated in FIG. 8, the first cooling fan 51 and the discharge fan 53 are caused to operate synchronously at least during the operation of the ultrasound treatment tool 2 and the second cooling fan 52 is caused to operate according to the temperature.

In the on-off control illustrated in FIG. 8, for example, a temperature sensor that is not illustrated in the drawing and that is arranged in the casing 30 of the drive device 3 measures a temperature T of the heatsink 50 and, based on the temperature T of the heatsink 50, the second cooling fan 52 is switched on from off or the second cooling fan 52 is switched off from on.

In other words, as illustrated in FIG. 8, at time t21, the drive controller 300 switches the ultrasound treatment tool 2 on from off to cause the ultrasound treatment tool 2 to start the operation and, at the same time, switches the first cooling fan 51 and the discharge fan 53 on from off to cause the first cooling fan 51 and the discharge fan 53 to start the operations. Then, when the temperature T of the heatsink 50 is at or higher than a given temperature Th1 because of the operation of the switching element 321 (time t22), the drive controller 300 switches the second cooling fan 52 on from off. Thereafter, when the temperature T of the heatsink 50 is lower than a given temperature Th2 (<Th1) because the second cooling fan 52 is caused to operate (time t23), the drive controller 300 switches the second cooling fan 52 off from on. In FIG. 8, at time t23, the drive controller 300 switches the ultrasound treatment tool 2 and the first cooling fan 51 off from on to cause the ultrasound treatment tool 2 and the first cooling fan 51 to stop the operations. At time t24 after elapse of a given time from time t23, the drive controller 300 then switches the discharge fan 53 off from on.

In the on-off control illustrated in FIG. 8, the second cooling fan 52 may be caused to operate after the given time elapses without measuring the temperature T of the heatsink 50 with the temperature sensor and without causing the second cooling fan 52 to operate for a given time from the start of operation of the ultrasound treatment tool 2 during which the temperature of the switching element 321 is relatively low to the rated temperature.

In other words, in the on-off control illustrated in FIG. 8, at time t21, the drive controller 300 switches the ultrasound treatment tool 2 on from off to cause the ultrasound treatment tool 2 to start the operation and, at the same time, switches the first cooling fan 51 and the discharge fan 53 on from off to cause the first cooling fan 51 and the discharge fan 53 to start the operations. At time t22 after the elapse of the given time from time t21, the drive controller 300 switches the second cooling fan 52 on from off to cause the second cooling fan 52 to start the operation. At time t23 after the elapse of the given time from time t22, the drive controller 300 switches the ultrasound treatment tool 2 off from on to stop the operation and switches the first cooling fan 51 and the second cooling fan 52 off from on. At time t24 after the elapse of the given time from time t23, the drive controller 300 switches the discharge fan 53 off from on.

In the on-off control illustrated in FIG. 8, because the second cooling fan 52 is not caused to operate during the given time from the start of operation of the ultrasound treatment tool 2 in which the temperature of the switching element 321 is relatively lower than the rated temperature, it is possible to ensure cooling performance without performing excessive cooling and reduce power consumption. Causing the discharge fan 53 to operate for the given time also after stopping the operation of the ultrasound treatment tool 2 makes it possible to discharge the warmed air in the casing 30 of the drive device 3 to the outside and lower the temperature in the casing 30.

Figure 9:
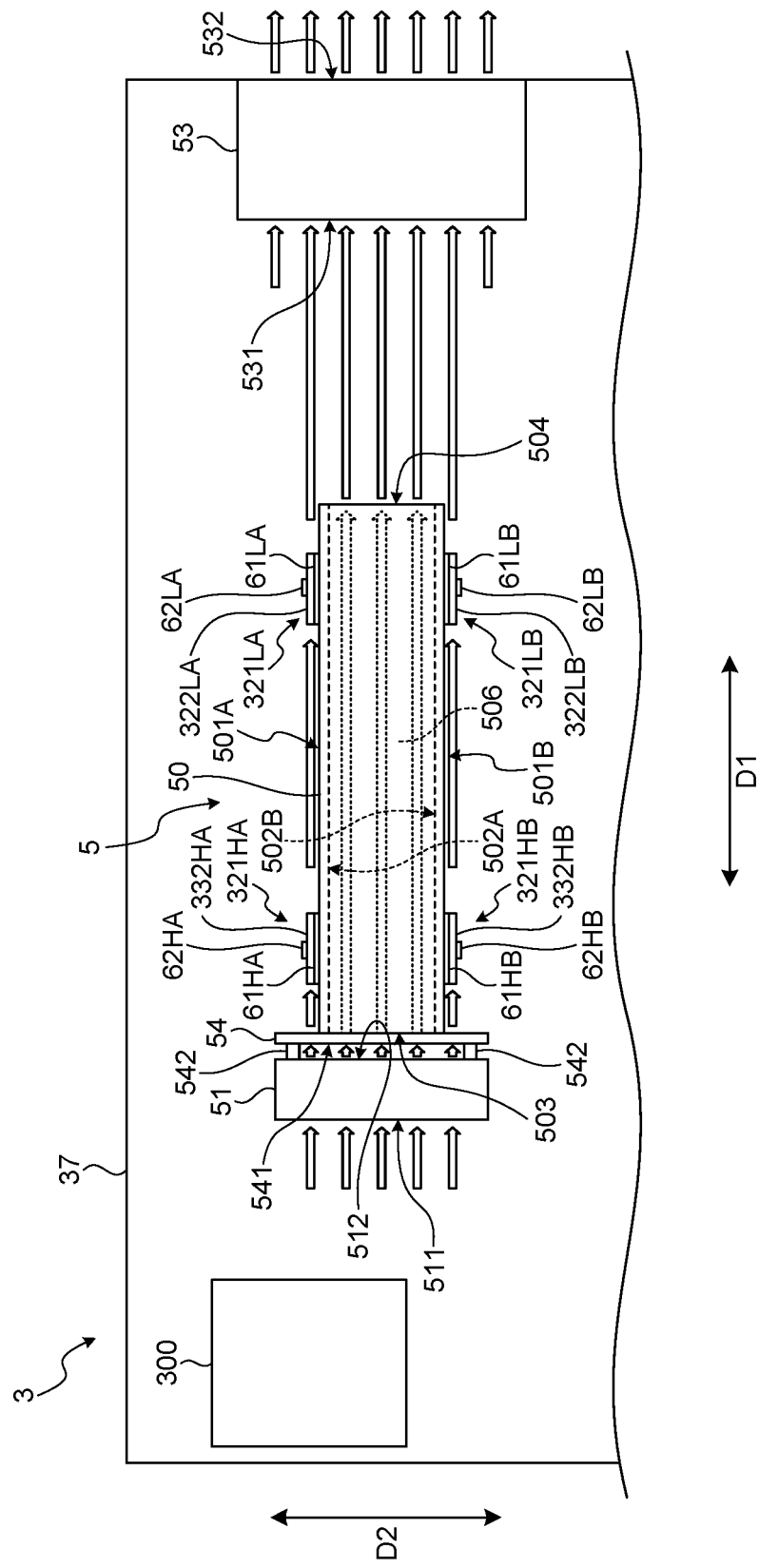
FIG. 9 is a plane view schematically illustrating a configuration of another example of the cooling device that is arranged in the drive device according to the first embodiment.

Note that, as illustrated in FIG. 3, as for the cooling device 5 of the first embodiment, the cooling device including the three fans that are the first cooling fan 51, the second cooling fan 52, and the discharge fan 53 has been described; however, the number of fans that are used to cool the switching elements 321 is not limited to three. For example, as illustrated in FIG. 9, only two fans that are the first cooling fan 51 and the discharge fan 53 may be included without arranging the second cooling fan 52 on the side of the second end of the heatsink 50 in the longitudinal direction D1 and between the heatsink 50 and the discharge fan 53. This makes it possible to reduce the number of parts and reduce the cost.

In the cooling device 5 according to the first embodiment, the first cooling fan 51 and the second cooling fan 52 are arranged respectively on the side of the first end of the heatsink 50 and on the side of the second end of the heatsink 50 in the longitudinal direction D1 such that air flows are generated from the side of the first end of the heatsink 50 to the side of the second end of the heatsink 50 in the longitudinal direction D1; however, the fans are not limited to this. For example, the heatsink 50 is divided into two parts that are a high side part where the high side switching elements 521HA and 521HB are positioned and a low side part where the switching elements 521LA and 521LB are positioned in the longitudinal direction D1 of the heatsink 50. A fan similar to the first cooling fan 51 may be arranged additionally between the high-side part and the low-side part to generate an airflow from the side of the first end of the heatsink 50 to the side of the second end of the heatsink 50 in the longitudinal direction D1.

Second Embodiment

A second embodiment of the drive device according to the disclosure will be described below. Note that description of the aspects common between the second embodiment and the first embodiment will be omitted as appropriate.

Figure 10:
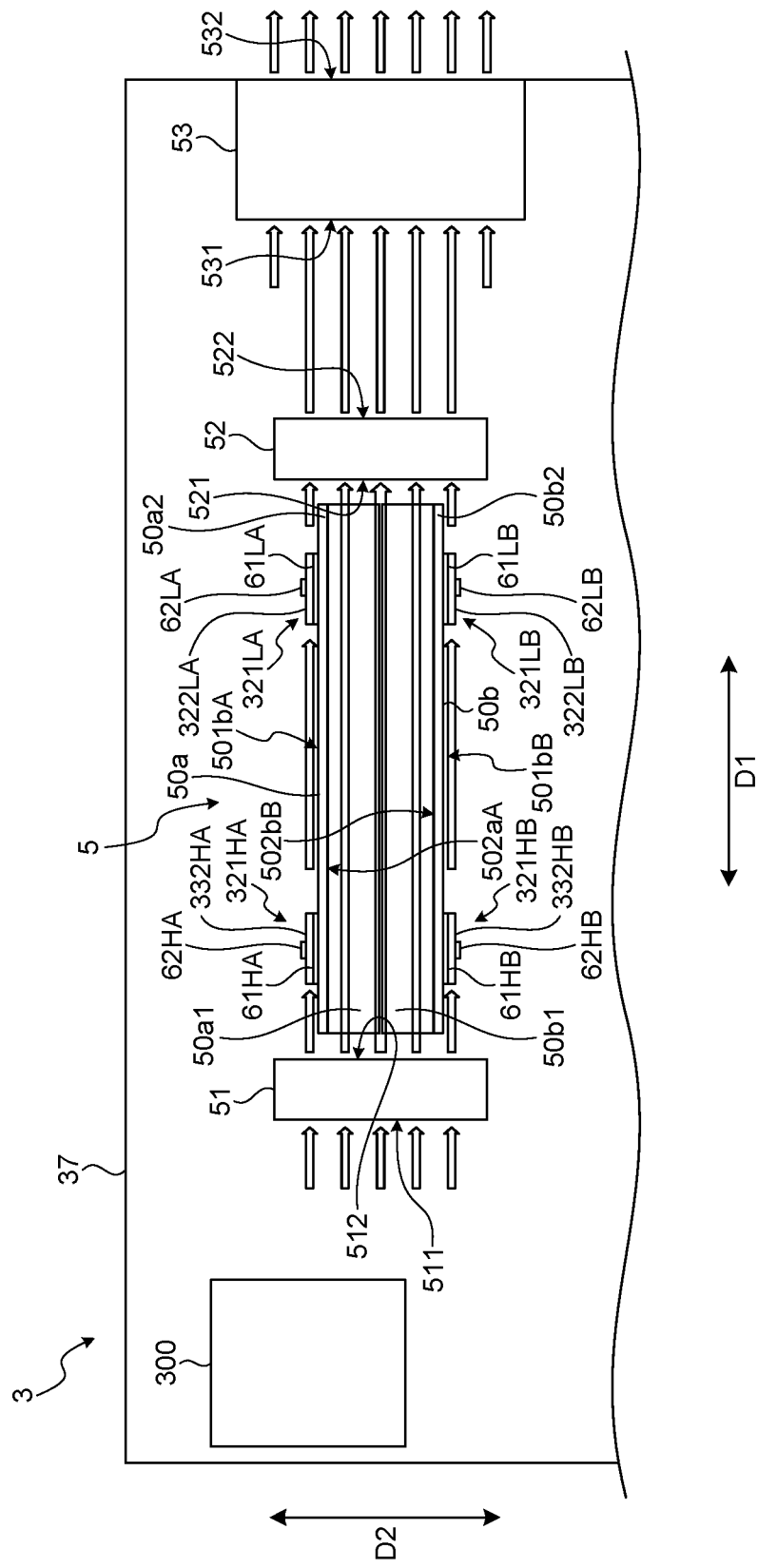
FIG. 10 is a plane view schematically illustrating an configuration of a cooling device that is arranged in a drive device according to a second embodiment.
Figure 11:
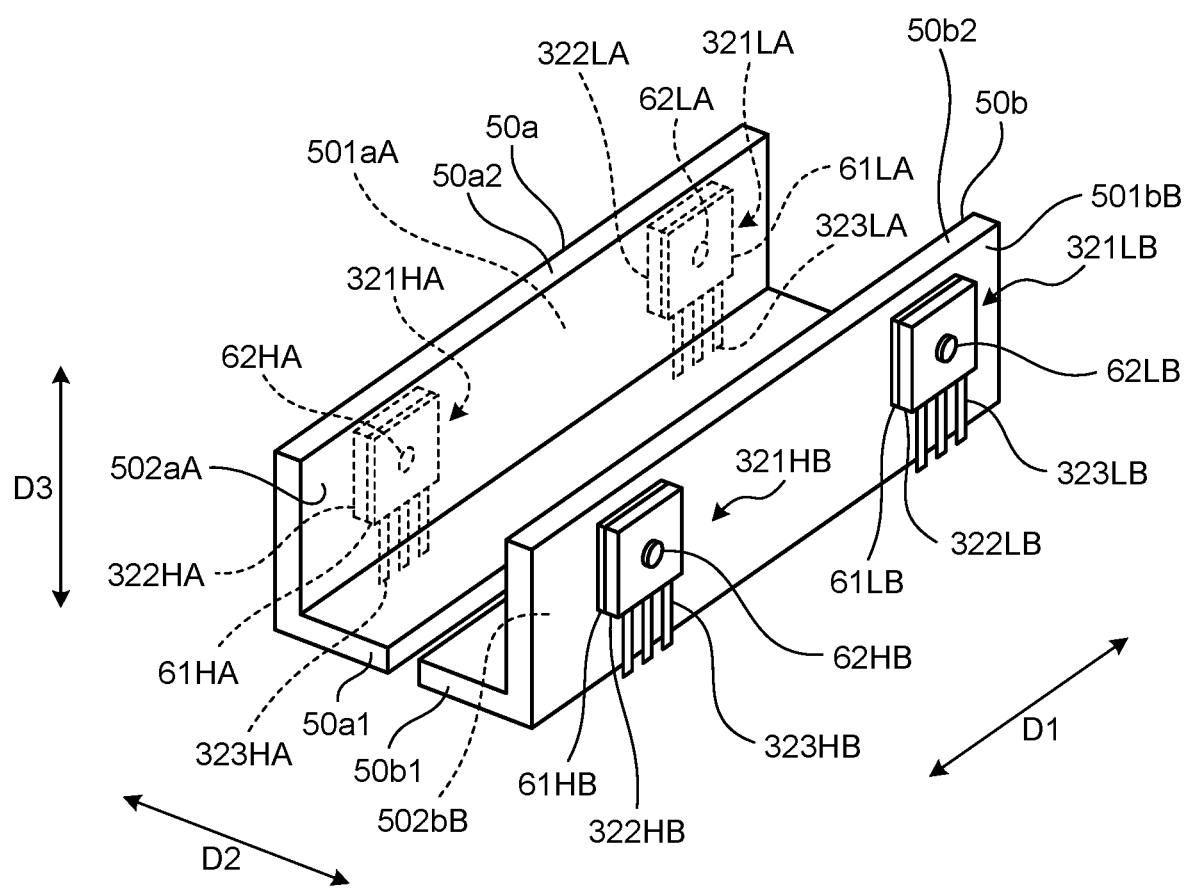
FIG. 11 is a perspective view illustrating a heatsink that is used for the cooling device according to the second embodiment.

FIG. 10 is a plane view schematically illustrating a configuration of the cooling device 5 that is arranged in the drive device 3 according to the second embodiment. FIG. 11 is a perspective view illustrating heatsinks 50a and 50b that are used in the cooling device 5 of the second embodiment.

The cooling device 5 that is arranged in the drive device 3 includes the heatsinks 50a and 50b in a pair that face respectively the switching elements 321 of the switching circuits 320A and 320B in a pair, the first cooling fan 51, the second cooling fan 52, and the discharge fan 53.

The heatsinks 50a and 50b consist of bottom plates 50a1 and 50b1 that are parallel to the circuit board 37 and side plates 50a2 and 50b2 that are arranged in an erecting manner in the heatsink height direction D3 from ends of the bottom plates 50a1 and 50b1 in the heatsink width direction D2 and the cross sections of the heatsinks 50a and 50b are L-shaped. The heatsinks 50a and 50b are fixed to the circuit board 37 in the state where the end faces of the ends of the respective bottom plates 50a1 and 50b1 on the side where the side plates 50a2 and 50b2 are not arranged in an erecting manner face each other with a given interval in between. The heatsinks 50a and 50b are formed using, for example, aluminum, aluminum alloy, copper, a copper alloy, or the like.

In the drive device 3 according to the second embodiment, because the heatsinks 50a and 50b whose cross sections are L-shaped are used, it is possible to reduce the material to be used to manufacture the heatsinks 50a and 50b and reduce the cost more than when a cuboid heatsink is used.

The element body 322HA of the switching element 321HA and the element body 322LA of the switching element 321LA are fixed to an outer surface 501aA of the side plate 50a2 by the screws 62HA and 62LA respectively via the radiation sheets 61HA and 61LA with which the element body 322HA and the element body 322LA are making contact. Note that an inner surface 502aA is formed on the back side of the outer surface 501aA of the side plate 50a2.

The element body 322HB of the switching element 321HB and the element body 322LB of the switching element 321LB are fixed to an outer surface 501bB of the side plate 50b2 by the screws 62HB and 62LB respectively via the radiation sheets 61HB and 61LB with which the element body 322HB and the element body 322LB are making contact. Note that an inner surface 502bB is formed on the back side of the outer surface 501bB in the side plate 50b2.

The first cooling fan 51 is arranged on a side of first ends of the heatsinks 50a and 50b in a longitudinal direction D1 with a given interval. The second cooling fan 52 is arranged on a side of second ends of the heatsinks 50a and 50b in the longitudinal direction D1 with a given interval. As described above, in the cooling device 5 of the second embodiment, without being fixed to the heatsinks 50a and 50b with fixing members, the first cooling fan 51 and the second cooling fan 52 are set in positions being away from the heatsinks 50a and 50b. Accordingly, it is possible to avoid the heatsinks 50a and 50b and the first cooling fan 51 and the second cooling fan 52 from making direct contact with each other, allow a wind to easily go out of the space that is formed between the heatsinks 50a and 50b and the first cooling fan 51 and the second cooling fan 52, and thus make heat less stagnant. The first cooling fan 51, the second cooling fan 52, and the discharge fan 53 are arranged such that their respective rotation axis lines are parallel to the longitudinal direction D1 of the heatsinks 50a and 50b and are on the same straight line.

In the cooling device 5 of the second embodiment, the heatsinks 50a and 50b and the switching elements 321HA, 321HB, 321LA and 321LB are positioned within each of projection planes of the first cooling fan 51, the second cooling fan 52, and the discharge fan 53 viewed along the longitudinal direction D1 (longitudinal axis) of the heatsinks 50a and 50b.

Operating the first cooling fan 51 forms an airflow along the outer surface 501aA of the heatsink 50a, an airflow along the inner surface 502aA of the heatsink 50a, an airflow along the outer surface 501b of the heatsink 50b, an airflow along the inner surface 502bB of the heatsink 50b, etc.

Accordingly, the heat of the heatsink 50a is radiated to the air flowing along each of the outer surface 501aA and the inner surface 502aA. This promotes radiation from the switching elements 321HA and 321LA to the heatsink 50a via the radiation sheets 61HA and 61LA, so that the switching elements 321HA and 321LA are cooled. Furthermore, because the airflows respectively along the outer surface 501aA and the inner surface 502aA are formed simultaneously, it is possible to radiate the heat of the heatsink 50a into the air efficiently more than in the case where an airflow along only any one of the outer surface 501aA and the inner surface 502aA is formed and resultantly cool the switching elements 321HA and 321LA efficiently.

Furthermore, in the cooling device 5 of the second embodiment, the airflow along the outer surface 501aA hits the switching elements 321HA and 321LA that are fixed to the outer surface 501aA. This makes it possible to promote not only radiation from the switching elements 321HA and 321LA to the heatsink 50a but also radiation from the switching elements 321HA and 321LA to the air and thus cool the switching elements 321HA and 321LA more efficiently.

The heat of the heatsink 50b is radiated to the air flowing along each of the outer surface 501bB and the inner surface 502bB. Accordingly, radiation from the switching elements 321HB and 321LB to the heatsink 50b via the radiation sheets 61HB and 61LB is promoted and the switching elements 321HB and 321LB are cooled. Furthermore, because the airflows along the outer surface 501bB and the inner surface 502bB are formed simultaneously, it is possible to radiate the heat of the heatsink 50b to the air efficiently more than in the case where an airflow along only any one of the outer surface 501bB and the inner surface 502bB is formed and resultantly cool the switching elements 321HB and 321LB efficiently.

Furthermore, in the cooling device 5 of the second embodiment, the airflow along the outer surface 501bB hits the switching elements 321HB and 321LB that are fixed to the outer surface 501bB. This makes it possible to promote not only radiation from the switching elements 321HB and 321LB to the heatsink 50b but also radiation from the switching elements 321HB and 321LB into the air and thus cool the switching elements 321HB and 321LB more efficiently.

As described, in the drive device 3 according to the second embodiment, cooling the heatsinks 50a and 50b and the switching elements 321 with the cooling device 5 makes it possible to inhibits the temperature of the switching elements 321 from increasing and thus cool the switching elements 321 efficiently.

Third Embodiment

A third embodiment of the drive device according to the disclosure will be described below. Note that description of the aspects common between the third embodiment and the first embodiment will be omitted as appropriate.

Figure 12:
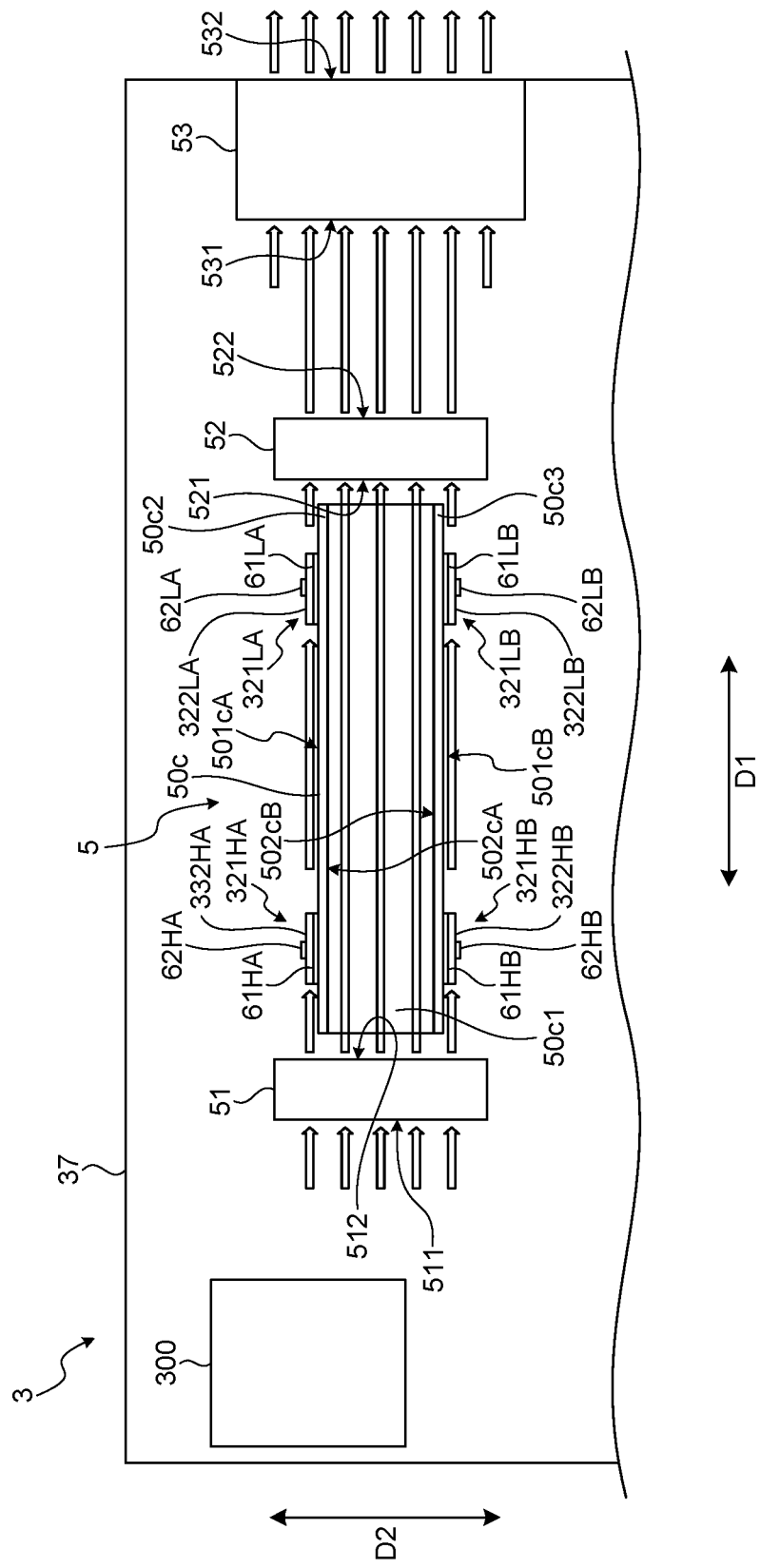
FIG. 12 is a plane view schematically illustrating a configuration of a cooling device that is arranged in a drive device according to a third embodiment.
Figure 13:
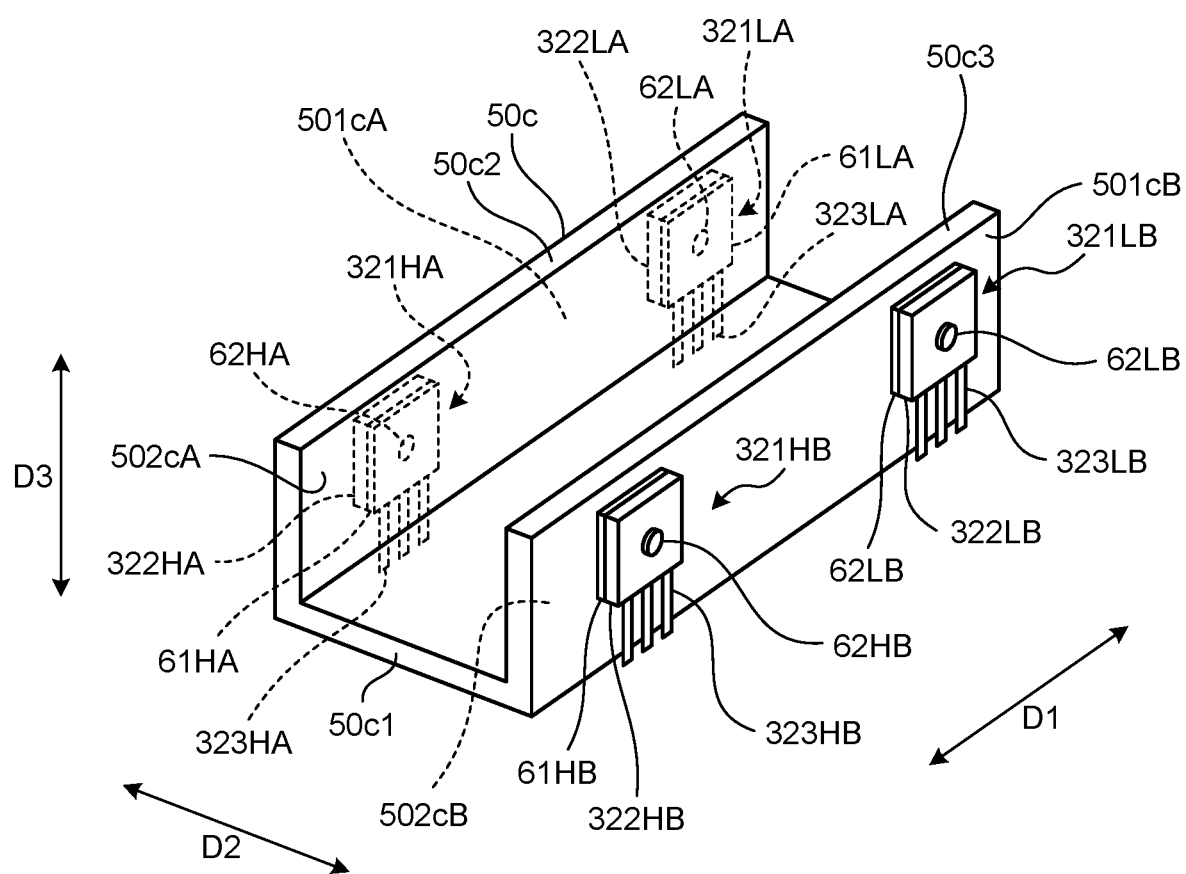
FIG. 13 is a perspective view illustrating a heatsink that is used for the cooling device according to the third embodiment.

FIG. 12 is a plane view schematically illustrating a configuration of the cooling device 5 that is arranged in the drive device 3 according to the third embodiment. FIG. 13 is a perspective view illustrating a heatsink 50c that is used in the cooling device 5 of the third embodiment.

The cooling device 5 of the third embodiment includes a single heatsink 50c, the first cooling fan 51, a second cooling fan 52, and the discharge fan 53.

The heatsink 50c consists of a bottom plate 50c1 that is parallel to the circuit board 37 and two side plates 50c2 and 50c3 that are arranged in an erecting manner from both ends of the bottom plate 50c1 and the bottom plate 50c1 is fixed to the circuit board 37. The heatsink 50c is formed using, for example, aluminum, aluminum alloy, copper, a copper alloy, or the like.

In the drive device 3 according to the third embodiment, because the heatsink 50c is used in the cooling device 5, it is possible to reduce the material that is used to manufacture the heatsink 50c and reduce the cost more than in the case where a cuboid heatsink is used. It is also possible to reduce the number of parts more than in the case where heatsinks whose cross-sections are L-shaped in a pair are used and improve workability in fixing the heatsink 50c to the circuit board 37.

The element body 322HA of the switching element 321HA and the element body 322LA of the switching element 321LA are fixed to an outer surface 501cA of the side plate 50c2 by the screws 62HA and 62LA respectively via the radiation sheets 61HA and 61LA with which the element body 322HA and the element body 322LA are making contact. Note that an inner surface 502cA is formed on the back side of the outer surface 501cA of the side plate 50c2.

The element body 322HB of the switching element 321HB and the element body 322LB of the switching element 321LB are fixed to an outer surface 501cB of the side plate 50c3 by the screws 62HB and 62LB respectively via the radiation sheets 61HB and 61LB with which the element body 322HB and the element body 322LB are making contact. Note that the inner surface 502cB is formed on the back side of the outer surface 501cB of the side plate 50c3.

The first cooling fan 51 is arranged on a side of a first end of the heatsink 50c in a longitudinal direction D1 with a given interval. The second cooling fan 52 is arranged on a side of a second end of the heatsink 50c in the longitudinal direction D1 with a given interval. The first cooling fan 51, the second cooling fan 52, and the discharge fan 53 are arranged such that their respective rotation axis lines are parallel to the longitudinal direction D1 of the heatsink 50c and are on the same straight line.

In the cooling device 5 of the third embodiment, the heatsink 50c and the switching elements 321HA, 321HB, 321LA and 321LB are positioned within each of projection planes of the first cooling fan 51 and the second cooling fan 52 viewed along the longitudinal direction D1 (longitudinal axis) of the heatsink 50c. Operating the first cooling fan 51 forms an airflow along the outer surface 501cA of the heatsink 50c, an airflow along the inner surface 502cA of the heatsink 50c, an airflow along the outer surface 501cB of the heatsink 50c, an airflow along the inner surface 502cB of the heatsink 50c, etc.

Accordingly, because the airflows respectively along the outer surface 501cA and the inner surface 502cA of the side plate 50c2 of the heatsink 50c are formed simultaneously, it is possible to radiate the heat of the side plate 50c2 into the air efficiently more than in the case where an airflow along only any one of the outer surface 501cA and the inner surface 502cA is formed and resultantly efficiently cool the switching elements 321HA and 321LA.

Furthermore, in the cooling device 5 of the third embodiment, the airflow along the outer surface 501aA hits the switching elements 321HA and 321LA that are fixed to the outer surface 501aA. This makes it possible to promote not only radiation from the switching elements 321HA and 321LA to the heatsink 50c but also radiation from the switching elements 321HA and 321LA into the air and thus cool the switching elements 321HA and 321LA more efficiently.

Furthermore, because airflows respectively along the outer surface 501cB and the inner surface 502cB of the side plate 50c3 of the heatsink 50c are formed simultaneously, it is possible to radiate the heat of the side plate 50c3 into the air efficiently more than in the case where an airflow along only any one of the outer surface 501cB and the inner surface 502cB is formed and resultantly cool the switching elements 321HB and 321LB more efficiently.

Furthermore, in the cooling device 5 of the third embodiment, the airflow along the outer surface 501cB hits the switching elements 321HB and 321LB that are fixed to the outer surface 501cB. This makes it possible to promote not only radiation from the switching elements 321HB and 321LB to the heatsink 50c but also radiation from the switching elements 321HB and 321LB to the air and thus cool the switching elements 321HB and 321LB more efficiently.

As described, in the drive device 3 according to the third embodiment, cooling the heatsink 50c and the switching elements 321 with the cooling device 5 makes it possible to inhibit the temperature of the switching elements 321 from increasing and thus inhibit the switching element 321 from being at the rated temperature or higher.

Fourth Embodiment

A fourth embodiment of the drive device according to the disclosure will be described below. Note that description of the aspects common between the fourth embodiment and the first embodiment will be omitted as appropriate.

FIG. 14 is a plane view schematically illustrating a configuration of the cooling device 5 that is arranged in the drive device 3 according to the fourth embodiment.

The cooling device 5 of the fourth embodiment includes the single heatsink 50, the first cooling fan 51, the second cooling fan 52, the discharge fan 53, and a guide plate 56. Note that the same heatsink 50 as that of the cooling device 5 of the first embodiment is used, the switching elements 321HA and 321LA are fixed to the outer surface 501A, and the switching elements 321HB and 321LB are fixed to the outer surface 501B. In the cooling device 5 of the fourth embodiment, the fixation plates 54 and 55 like those arranged in the cooling device 5 of the first embodiment are not attached on the side of the first end of the heatsink 50 and on the side of the second end of the heatsink 50 in the longitudinal direction D1.

The rotation axis line of the first cooling fan 51 is orthogonal to the longitudinal direction D1 of the heatsink 50. Thus, the outlet 512 of the first cooling fan 51 is oriented in the heatsink width direction and does not face the air inlet 503 of the heatsink 50. The second cooling fan 52 and the discharge fan 53 are arranged such that their rotation axis lines are parallel to the longitudinal direction D1 of the heatsink 50 and are positioned on the same straight line. The second cooling fan 52 is arranged with a given interval on the side of the second end of the heatsink 50 in the longitudinal direction D1 such that the inlet 521 of the second cooling fan 52 and the air outlet 504 of the heatsink 50 face each other. The heatsink 50 and the switching elements 321HA, 321HB, 321LA and 321LB are positioned within each of projection planes of the second cooling fan 52 and the discharge fan 53 viewed along the longitudinal direction D1 (longitudinal axis) of the heatsink 50.

The guide plate 56 that guides part of the air that goes out of the outlet 512 of the first cooling fan 51 toward the side of the first end of the heatsink 50 in the longitudinal direction D1 is arranged on the side of the first end of the heatsink D1 in the longitudinal direction D1. The guide plate 56 changes the orientation of the airflows by approximately 90 degrees from the outlet 512 of the first cooling fan 51 to the air inlet 503 of the heatsink 50; however, the angle by which the orientation of airflows is changed is not limited to this.

In the cooling device 5 of the fourth embodiment, the heatsink 50 and the switching elements 321HA, 321HB, 321LA and 321LB are positioned within a projection plane of the guide plate 56 viewed along the longitudinal direction D1 (longitudinal axis) of the heatsink 50. Accordingly, part of the air that goes out of the outlet 512 of the first cooling fan 51 is guided by the guide plate 56 toward the side of the first end of the heatsink 50 in the longitudinal direction D1 and thus an airflow along the outer surface 501A of the heatsink 50, an airflow along the outer surface 501 of the heatsink 50, and an airflow along the ventilation paths 506 of the heatsink 50 are formed.

Accordingly, in the cooling device 5 of the fourth embodiment, as in the cooling device 5 of the first embodiment, it is possible to simultaneously form airflows respectively along the outer surfaces 501A and 501B and the inner surfaces 502A and 502B of the heatsink 50. Furthermore, it is possible to cause part of the air that is guided by the guide plate 56 from the first cooling fan 51 to hit not only the heatsink 50 but also the switching elements 321HA, 321HB, 321LA and 321LB. Thus, the cooling device 5 of the fourth embodiment is able to cool the switching elements 321HA, 321HB, 321LA and 321LB efficiently.

As described above, in the drive device 3 according to the fourth embodiment, cooling the heatsink 50 and the switching elements 321 with the cooling device 5 makes it possible to inhibit the temperature of the switching element 321 from increasing and inhibit the switching element 321 from being at a rated temperature or higher.

In the cooling device 5 of the fourth embodiment, employing a configuration in which the guide plate 56 guides part of the air that goes out of the outlet 512 of the first cooling fan 51 to the side of the first end of the heatsink 50 in the longitudinal direction D1 makes it possible to increase freedom in layout of arrangement of the first cooling fan 51.

INDUSTRIAL APPLICABILITY

According to the disclosure, it is possible to provide a drive device capable of inhibiting the temperature of the device from increasing when driving a high-frequency treatment tool using drive energy of a high output.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A drive device comprising:
   a drive signal generator configured to generate a pair of drive signals for driving a high-frequency treatment tool that is electrically connected to the drive signal generator;
   a pair of buffer circuits each configured to input respective ones of the pair of drive signals;
   a pair of switching circuits configured to repeatedly turn on and off the pair of drive signals that are output from the pair of buffer circuits at a drive frequency for driving the high-frequency treatment tool or higher;
   a first radiation material that has a longitudinal axis and that is arranged to face one of the pair of switching circuits;
   a second radiation material that has a longitudinal axis and that is arranged to face another one of the pair of switching circuits;
   a fan configured to generate an airflow; and
   a casing configured to house the drive signal generator, the pair of switching circuits, the first radiation material, the second radiation material, and the fan,
   wherein the pair of switching circuits, the first radiation material, and the second radiation material are positioned within a projection plane of the fan viewed along the longitudinal axes of the first radiation material and the second radiation material,
   wherein the first radiation material is rectangular, and
   wherein the fan is configured to simultaneously form airflows respectively along two outward-facing planes of the first radiation material and two inward-facing planes of the first radiation material.

2. The drive device according to claim 1, wherein the fan is spaced at least a predetermined distance from the first radiation material.

3. The drive device according to claim 1, wherein the first radiation material and the second radiation material are components of a heatsink.

4. A drive device comprising:
   a drive signal generator configured to generate a pair of drive signals for driving a high-frequency treatment tool that is electrically connected to the drive signal generator;
   a pair of buffer circuits each configured to input respective ones of the pair of drive signals;
   a pair of switching circuits configured to repeatedly turn on and off the pair of drive signals that are output from the buffer circuits at a drive frequency for driving the high-frequency treatment tool or higher;
   a first radiation material that has a longitudinal axis and that is arranged to face the pair of switching circuits;
   a fan configured to generate an airflow; and
   a casing configured to house the drive signal generator, the pair of switching circuits, the first radiation material, and the fan,
   wherein the pair of switching circuits and the first radiation material are positioned within a projection plane of the fan viewed along the longitudinal axis of the first radiation material,
   the first radiation material is cylindrical,
   the first radiation material includes
      a first opening that is formed on a side of a first end of the longitudinal axis of the first radiation material;
      a second opening that is formed on a side of a second end that is another end of the longitudinal axis of the first radiation material; and
      a passage communicating between the first opening and the second opening,
   one of the pair of switching circuits is arranged such that the one switching circuit faces an outer circumferential surface of the first radiation material, and
   the one switching circuit and another of the pair of the switching circuits face each other in a direction orthogonal to the longitudinal axis with the first radiation material interposed in between.

5. The drive device according to claim 4, wherein the fan is spaced at least a predetermined distance from the first radiation material.

6. A drive device comprising:
   a drive signal generator configured to generate a pair of drive signals for driving a high-frequency treatment tool that is electrically connected to the drive signal generator;
   a pair of buffer circuits each configured to input respective ones of the pair of drive signals;
   a pair of switching circuits configured to repeatedly turn on and off the pair of drive signals that are output from the pair of buffer circuits at a drive frequency for driving the high-frequency treatment tool or higher;
   a first radiation material that has a longitudinal axis and that is arranged to face one of the pair of switching circuits;
   a second radiation material that has a longitudinal axis and that is arranged to face another one of the pair of switching circuits;
   a fan configured to generate an airflow; and
   a casing configured to house the drive signal generator, the pair of switching circuits, the first radiation material, the second radiation material, and the fan,
   wherein the pair of switching circuits, the first radiation material, and the second radiation material are positioned within a projection plane of the fan viewed along the longitudinal axes of the first radiation material and the second radiation material and
   wherein the first radiation material includes a fixation material that is disposed at an end of the longitudinal axis of the first radiation material, the fixation material being configured to fix the fan.

7. The drive device according to claim 6, wherein the fan is spaced at least a predetermined distance from the first radiation material.

8. The drive device according to claim 6, wherein the first radiation material and the second radiation material are components of a heatsink.

9. A drive device comprising:
   a drive signal generator configured to generate a pair of drive signals for driving a high-frequency treatment tool that is electrically connected to the drive signal generator;

a pair of buffer circuits each configured to input respective ones of the pair of drive signals;
a pair of switching circuits configured to repeatedly turn on and off the pair of drive signals that are output from the pair of buffer circuits at a drive frequency for driving the high-frequency treatment tool or higher;
a first radiation material that has a longitudinal axis and that is arranged to face one of the pair of switching circuits;
a second radiation material that has a longitudinal axis and that is arranged to face another one of the pair of switching circuits;
a fan configured to generate an airflow; and
a casing configured to house the drive signal generator, the pair of switching circuits, the first radiation material, the second radiation material, and the fan,
wherein the pair of switching circuits, the first radiation material, and the second radiation material are positioned within a projection plane of the fan viewed along the longitudinal axes of the first radiation material and the second radiation material
wherein the fan is arranged on a side of a first end of the longitudinal axis of the first radiation material, and
wherein the drive device further includes a discharge fan that is arranged on a side of a second end of the longitudinal axis of the first radiation material, the second end being opposite the first end, the discharge fan being configured to discharge air from an inside of the casing to an outside.

10. The drive device according to claim 9, further comprising a drawing fan that is arranged on the side of the second end of the longitudinal axis of the first radiation material and between the first radiation material and the discharge fan, the drawing fan being configured to draw the airflow that is generated by the fan.

11. The drive device according to claim 10, wherein a longitudinal axis of the drawing fan and a longitudinal axis of the discharge fan are substantially perpendicular to the longitudinal axis of the first radiation material, and a longitudinal extent of the discharge fan is larger than a longitudinal extent of the drawing fan.

12. The drive device according to claim 9, wherein the fan and the discharge fan are caused to operate synchronously and the drawing fan is caused to operate according to a temperature of the first radiation material.

13. The drive device according to claim 9, wherein the fan is spaced at least a predetermined distance from the first radiation material.

14. The drive device according to claim 9, wherein the first radiation material and the second radiation material are components of a heatsink.

* * * * *